United States Patent [19]

Phillips et al.

[11] Patent Number: 4,673,387
[45] Date of Patent: Jun. 16, 1987

[54] PELLET INJECTOR

[75] Inventors: Ian R. Phillips, Killara; Robert H. Lodge; Glen W. Bunyan, both of Dee Why, all of Australia

[73] Assignee: N. J. Phillips Pty. Limited, Dee Why, Australia

[21] Appl. No.: 858,065

[22] Filed: Apr. 30, 1986

[30] Foreign Application Priority Data

May 6, 1985 [AU] Australia .............................. PH0437

[51] Int. Cl.⁴ ........................................... A61M 31/00
[52] U.S. Cl. ..................................................... 604/62
[58] Field of Search ....................... 604/61, 62, 63, 64, 604/57, 59, 218; 221/78, 79, 81, 88

[56] References Cited

U.S. PATENT DOCUMENTS

| 3,520,299 | 7/1970 | Lott et al. | 604/62 |
| 3,669,104 | 6/1972 | Wyatt et al. | 604/62 X |
| 3,774,607 | 11/1973 | Schmitz | 604/62 |
| 4,077,406 | 3/1978 | Sandhage et al. | 604/62 X |
| 4,576,591 | 3/1986 | Kaye et al. | 604/62 |

Primary Examiner—John D. Yasko
Attorney, Agent, or Firm—Ladas & Parry

[57] ABSTRACT

An injector to dispense pellets from a magazine rotatably supported in the injector, the injector has an indexing mechanism which causes indexing of the magazine, with the indexing mechanism being actuated by an injection rod which injects the pellets, and with the indexing operation taking place upon return of the indexing rod to its rest position.

10 Claims, 4 Drawing Figures

PELLET INJECTOR

The present invention relates to injectors to deliver pellets and more particularly but not exclusively to injectors to implant pellets in animals.

The implantation of solid pellets under the skin of animals can be a desirable form of dispensing some medications. However previous devices to implant or inject pellets have generally been complex thereby making them unreliable and expensive to manufacture.

Previous devices to implant pellets beneath the skin of animals are described in U.S. Pat. Nos. 3,774,607, 4,077,406, 4,447,223, 4,403,610, 3,669,104 and 3,520,299. Of these previous devices all but two, that is the devices disclosed in U.S. Pat. No. 4,447,223 and applicant's earlier U.S. Pat. No. 4,403,610, either have no indexing mechanism or cause indexing of the magazine on the forward stroke of the injecting rod. These previous devices have generally been complex and since indexing takes place on the indexing stroke of the rod, damage can occur if indexing has not been complete. U.S. Pat. Nos. 4,447,223 and 4,403,610 disclose devices which cause indexing on the reverse stroke of the injection rod. However the indexing mechanism is generally complex since a separate indexing rod is employed to cause indexing. This accordingly adds to the complexity of the device and the cost of manufacture, as well as detracts from the reliability thereof.

It is the object of the present invention to overcome or substantially ameliorate the above disadvantages.

There is disclosed herein an injector to dispense pellets from a magazine to be supported by the injector, said magazine having a plurality of spaced pellet receiving parallel passages extending therethrough, said injector comprising a body, an injector rod slidably mounted in said body so as to be movable along a predetermined path from a retracted position to an inject position, said body having a mounting to support said magazine, said mounting being positioned to locate said magazine with one of said passages extending along said path so that said injector rod passes through said magazine so as to move a pellet therefrom to be injected, an operator manipulable trigger mounted on said body and operatively associated with said rod to cause movement thereof along said path and indexing means actuated by said rod to cause indexing of said magazine, said indexing means including an indexing link movably mounted on said body and movable in a plane generally transverse of said path, said link being positioned to be engaged by said rod and to be moved thereby between a first position with said link projecting into said path and a second position clear of said path, means biassing said link to said first position, and ratchet means connected to said link so as to move therewith, said ratchet means being biassed to engage said magazine to cause indexing thereof when said link is moved from said second position to said first position.

A preferred form of the present invention we now have described by way of example with reference to the accompanying drawings wherein.

Figure 1:
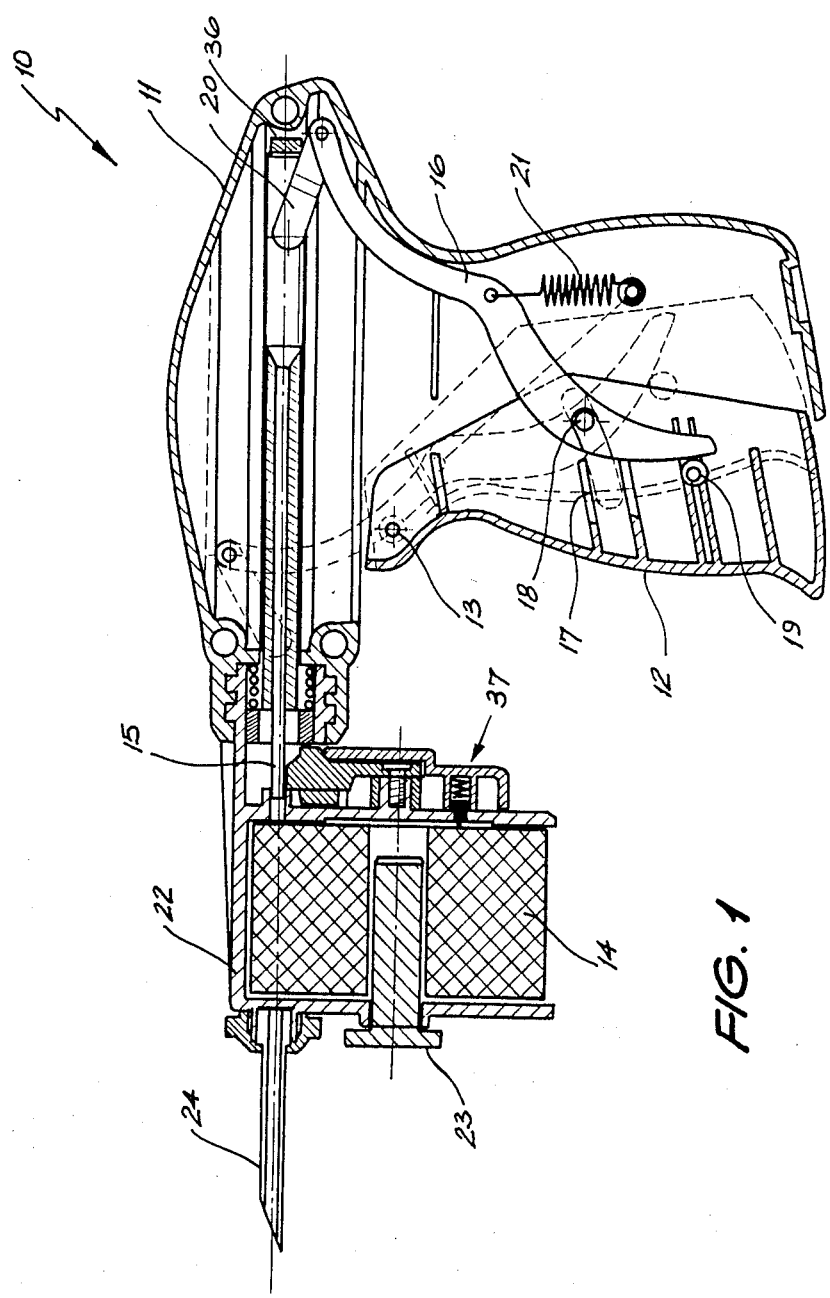
FIG. 1 is a schematic path section side elevation of an injector to implant pellets.
Figure 2:
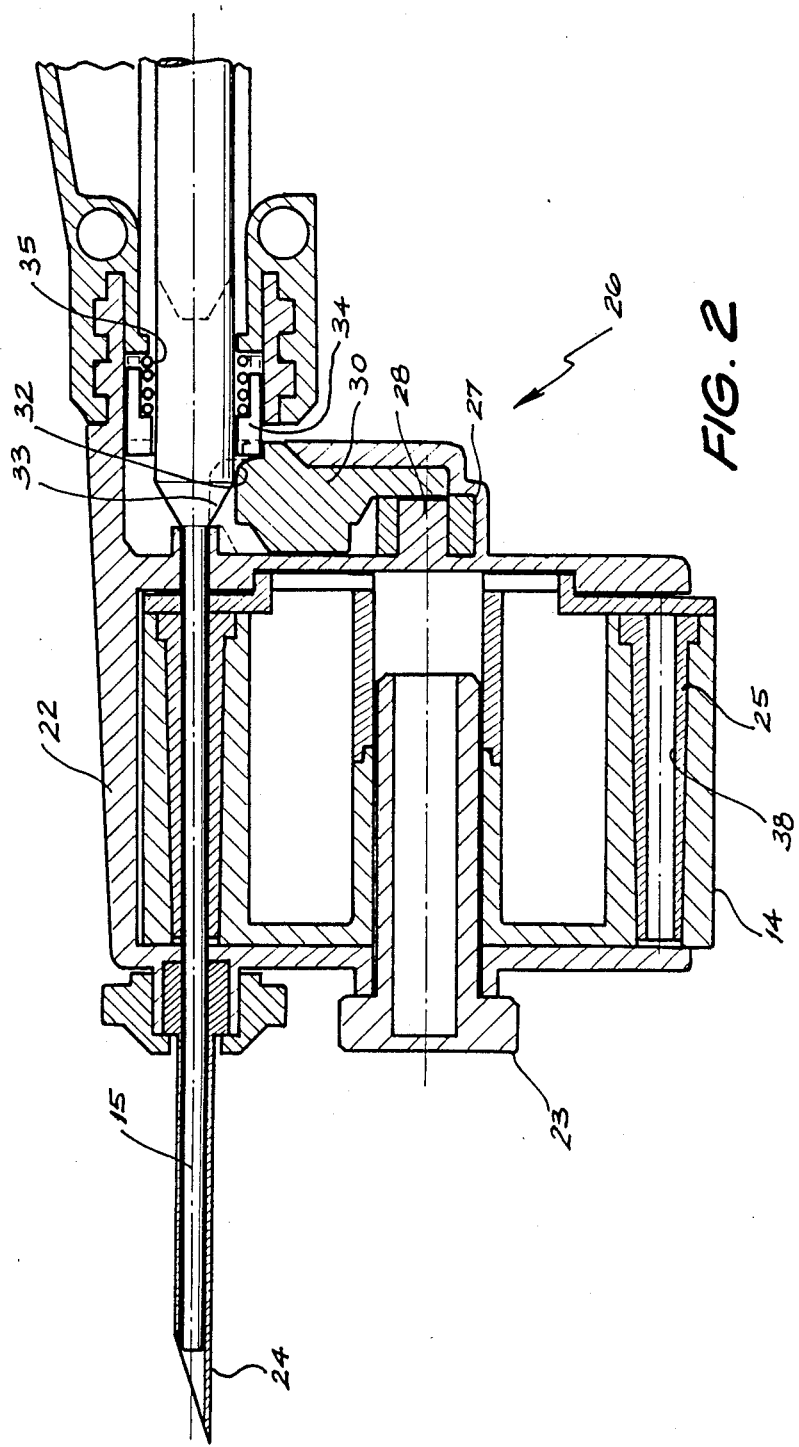
FIG. 2 is a schematic section side elevation of a portion of the injector of FIG. 1.

In the accompanying drawing there is schematically depicted an injector 10 to inject pellets beneath the skin of animals. The pellets may contain therapeutic agents, hormones, or antibiotics. The injector 10 has a body 11 which pivotally supports an operator manipulated trigger 12 via a pin 13. Also supported by the body 11 is a cylindrical magazine 14 which receives the pellets to be injected. Slidably mounted within the body 11 is an injector rod 15 which is movable along a generally linear path from a retracted position (as seen in FIG. 1) to an injecting position as seen in FIG. 2. The rod 15 is operatively associated with the trigger 12 by means of a first link 16 which is moved by the trigger 12 by the co-operation of a pair of slots 17 slidably receiving a pin 18. The pin 18 is fixed to the first link 16 so as to pivotally support the link 16, while being fixed to the body 11. Additionally one end of the first link 16 slidably abuts a pin 19. The other end of the first link 16 is pivotally attached to a second link 20 which is pivotally attached to one extremity of the injector rod 15. The first link 16 is biased by spring 21 to move the rod 15 to the retracted position.

The forward end of the injector 10 is provided with a magazine housing 22 which receives a magazine retainer 23 about which the magazine 14 rotates. The magazine housing 22 is provided with an injector needle 24 through which the pellet is delivered by the injector rod 15. More particularly, the injector rod 15 passes along a predetermined path extending through the magazine 15.

Figure 4:
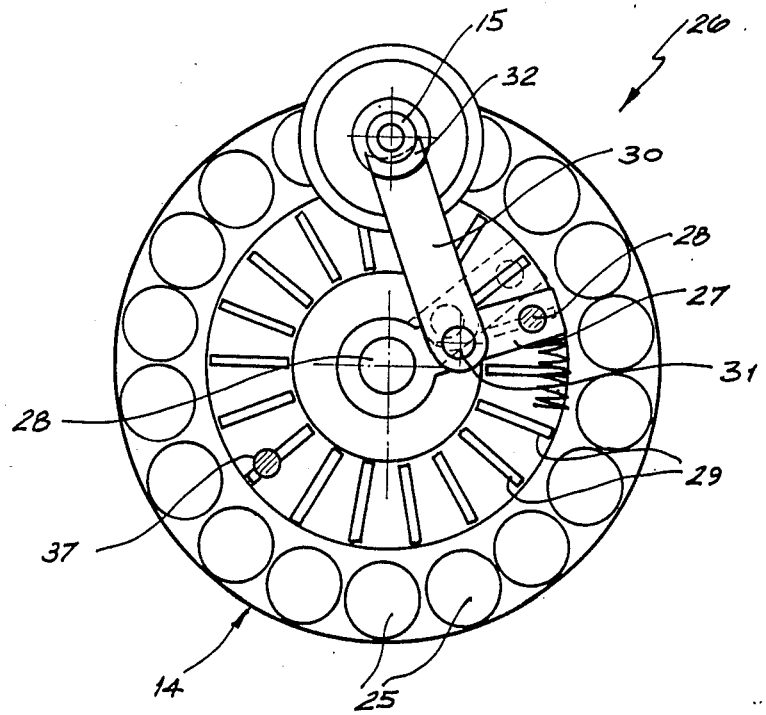
FIG. 4 is a schematic end elevation of the magazine and indexing mechanism employed in the injector of FIG. 1.

As can be seen from FIG. 4 the magazine 14 is provided with a plurality of passages 25 within which the pellets are frictionally held.

Figure 3:
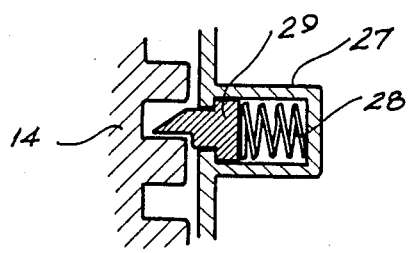
FIG. 3 is a schematic section side elevation of an indexing ratchet employed in the injector of FIG. 1.

The magazine 14 is indexed by means of an indexing assembly 26 best seen in FIGS. 2 and 4. The indexing assembly 26 includes an indexing arm 27 pivotally supported by an axle 28 formed in the magazine housing 22. The indexing arm 27 is provided with an indexing ratchet 29 resiliently biased by spring 28 into engagement with the indexing pawls 29 formed on one face of the magazine 14. The indexing arm 27 is caused to angularly oscillate in co-operation with the injection rod 15 via an indexing link 30. The indexing link 30 is pivotally attached at its lower end by a pin 31 to the indexing arm 27. The other end of the indexing link 30 is provided with a shaped end 32 which slidably engages an inclined surface 33 on the injection rod 15. As the injection rod 15 passes from the retracted position to the extended position the inclined surface 33 engages the end 32 of the indexing link 30 causing movement thereof to pivot the indexing arm 27. The indexing arm 27 pivots to the next pawl 29. There is further provided a retaining member 34 which engages the indexing link 30 to selectively prevent return thereof to its initial start position. The retaining member 34 is biased to a retaining position in respect of the indexing link 30 by means of a spring 35, while the retaining member 34 is also provided with a release slide 36. As the indexing rod 15 returns to its retracted position, the release slide 36 is engaged causing retraction of the retaining member 34 to thereby release the indexing link 30. Upon release of the indexing link 30, the link 30 is caused to move under the influence of a spring (not depicted) to cause indexing of the magazine 14. There is further provided a non return pawl assembly 37 of similar construction to the pawl assembly of FIG. 3, and adapted to allow movement of the magazine 14 in the indexing direction only.

To locate each of the pellets within its respective passage 25 there is provided a pellet cartridge 38.

What we claim is:

1. An injector to dispense pellets from a magazine to be supported by the injector, said magazine having a plurality of spaced pellet receiving parallel passages extending therethrough, said injector comprising a body, an injector rod slidably mounted in said body so as to be movable along a predetermined path from a retracted position to an inject position, said body having a mounting to support said magazine, said mounting being positioned to locate said magazine with one of said passages extending along said path so that said injector rod passes through said magazine so as to move a pellet therefrom to be injected, an operator manipulable trigger mounted on said body and operatively associated with said rod to cause movement thereof along said path, and indexing means actuated by said rod to cause indexing of said magazine, said indexing means including an indexing link movably mounted on said body and movable in a plane generally transverse of said path, said link being positioned to be engaged by said rod and to be moved thereby between a first position with said link projecting into said path and a second position clear of said path, means biassing said link to said first position, and ratchet means connected to said link so as to move therewith, said ratchet means being biassed to engage said magazine to cause indexing thereof when said link is moved from said second position to said first position.

2. The injector of claim 1 wherein said indexing means further includes an indexing arm pivotally supported on said body so as to be pivotable about an axis generally parallel to said path, pivot means pivotally connecting said link and said arm so that movement of said link causes pivoting of said arm, and wherein said ratchet means is mounted on the extremity of said arm remote from said pivot means.

3. The injector of claim 2 wherein said magazine is pivotally mounted so as to be rotatable about an axis parallel to said path but spaced therefrom, and said arm is pivotally mounted so as to pivot about the axis of said magazine.

4. The injector of claim 1 further including a retaining member movable between a retaining position engaging said link and preventing movement thereof from the second to the first positions thereof, and a release position allowing movement of said link, and means to cause movement of said retaining member from the retaining position to the release position as said rod moves from the inject position to the retract position.

5. The injector of claim 4 including a release slide slidably mounted in said body so as to extend generally parallel to and adjacent said rod, said release slide being positioned to engage said retaining member to cause the movement thereof to said release position, and being engaged by said rod as it is moved. from said inject position to said retract position.

6. The injector of claim 5 further including means biassing said retaining member to the retaining position thereof.

7. A magazine to be used with the injector of claim 1, said magazine being of cylindrical configuration and having a plurality of longitudinally extending pellet receiving passages equally angularly arranged about the axis of the magazine and at a fixed radius relative thereto, and a plurality of indexing projections equally angularly spaced about the longitudinal axis of the magazine and adapted to be engaged by the ratchet means of said injector, with the number of said passages being equal to the number of said projections.

8. The magazine of claim 7 wherein said projections are equiangularly spaced between adjacent passages.

9. An injector to dispense pellets from a magazine to be supported by the injector, said magazine having a plurality of spaced pellets receiving parallel passages extending therethrough, said injector comprising a body, an injector rod slidably mounted in said body so as to be movable along a predetermined path from a retracted position to an inject position, said body having a mounting to support said magazine, said mounting being positioned to locate said magazine with one of said passages extending along said path so that said injector rod passes through said magazine so as to move a pellet therefrom to be injected, an operator manipulable trigger mounted on said body and operatively associated with said rod to cause movement thereof along said path and indexing means actuated by said rod to cause indexing of said magazine, said indexing means including an indexing link movably mounted on said body and movable in a plane generally transverse of said path, said link being positioned to be engaged by said rod and to be moved thereby between a first position with said link projecting into said path and a second position clear of said path, means biassing said link to said first position, and ratchet means connected to said link so as to move therewith, said ratchet means being biassed to engage said magazine to cause indexing thereof when said link is moved in a first direction between the first and second positions of said link, while said magazine remains stationary during movement of said link in the opposite direction to said first direction between the first and second positions of said link.

10. The injector of claim 9 wherein said link is moved in said first direction when moving from said second position to said first position of said link.

* * * * *